United States Patent [19]

Miyoshi

[11] Patent Number: 4,792,524

[45] Date of Patent: Dec. 20, 1988

[54] ADULT T CELL LEUKEMIA ASSOCIATED CELL STRAIN

[75] Inventor: Isao Miyoshi, Kouchi, Japan

[73] Assignee: Eisai Co., Ltd., Tokyo, Japan

[21] Appl. No.: 70,135

[22] Filed: Jul. 2, 1987

Related U.S. Application Data

[63] Continuation of Ser. No. 576,661, Feb. 3, 1984, abandoned.

[30] Foreign Application Priority Data

Feb. 18, 1983 [JP] Japan ................. 58-24548

[51] Int. Cl.$^4$ ............... C12N 5/00; C12N 7/00; A61K 37/00
[52] U.S. Cl. ............... 435/240.2; 435/5; 435/235; 435/237; 435/948; 424/89; 424/93; 935/57; 935/60; 935/65; 935/70
[58] Field of Search ............... 435/5, 29, 235–239, 435/172.2, 240.2, 240.21, 948; 424/89, 93; 935/32, 57, 60, 65, 70, 95, 96, 99, 101, 102, 105, 106, 109

[56] References Cited

U.S. PATENT DOCUMENTS

| | | | |
|---|---|---|---|
| 4,442,205 | 4/1984 | Hamer et al. | 935/70 |
| 4,464,465 | 8/1984 | Lostrum | 935/71 |
| 4,588,681 | 5/1986 | Sawada et al. | |

FOREIGN PATENT DOCUMENTS

| | | | |
|---|---|---|---|
| 2487201 | 1/1982 | France | 424/88 |
| 2122343 | 1/1984 | United Kingdom | |

OTHER PUBLICATIONS

Salahuddin et al. (1983), Virology, vol. 129, pp. 51–64.
Chen et al. (11-1983), Proc. Natl. Acad. Sci., USA, vol. 80, pp. 7006–7009.
Yamamoto et al. (8-1982), Science, vol. 217, pp. 737–739.
Koyanagi et al. (1984), J. Gen. Virol., vol. 65, pp. 1781–1789.
Miyoshi, I. et al, Nature, 294:770-771 (12-1981).
Essex, M., Journal of the National Cancer Institute, 69:981-985 (10-1982).
Hinuma, Y. et al, Proc. Natl. Acad. Sci., USA; 76(10); 6476-6480 (10-1981).
Miyoshi, I. et al, The Lancet, May 1, 1982, p. 1016.
FEBS Lett, 1984, 177(2), pp. 200–204.
Chemical Abstracts, Kobayashi et al, vol. 101, 1984, #66926s.
Chemical Abstracts, Hoshina et al, vol. 102, 1985, #1329a.
Chemical Abstracts, Okai et al, vol. 102, 1985, #43754r.

*Primary Examiner*—Margaret Moskowitz
*Attorney, Agent, or Firm*—Flynn, Thiel, Boutell & Tanis

[57] ABSTRACT

An adult T call leukemia associated cell strain can be obtained from a mixed culture of leukocytes of a rabbit and adult T cell leukemia associated antigen producing cells.

7 Claims, No Drawings

ADULT T CELL LEUKEMIA ASSOCIATED CELL STRAIN

This application is a continuation of application Ser. No. 576,661, filed on Feb. 3, 1984, now abandoned.

The invention relates to an adult T cell leukemia associated cell strain, a process for production of the same and a process for producing an adult T cell leukemia associated antiserum by inoculating said cell strain into an animal.

Adult T cell leukemia is a recently identified form of leukemia described by Kozuki et al. in 1977. Clinically, this disease attacks adult human beings and is characterized by leukemia T cells having an irregular or segmented nucleus and lymph node enlargement and hepatosplenomegaly. In many cases, it proceeds subacutely and often causes formation of a dermatopathial lesion. Generally, lymphatic leukemia affects infant human beings, is mostly of a non-T, non-B type. Adult T cell leukemia exclusively affects adults and is typified by morbid cells having the surface character of peripheral T cells.

This disease has a tendency to occur in Kyushu and Southern Shikoku, and it is reported that many patients who suffer from this disease in Tokyo or Osaka come from the Kyushu or Shikoku districts.

As will be mentioned below, it is known that this disease is caused by the infection of a virus, the so-called adult T cell leukemia virus, hereinafter referred to as ATLV. It is thus possible to determine a local distribution of antibody-positive persons by detecting the adult T cell leukemia associated antibody which develops in persons who become infected with the virus.

The result of a previous investigation showed that patients affected with this disease are found mostly in Kyushu and Shikoku and also are distributed throughout Okinawa and the Kii Peninsula. It was further found that this disease follows certain family lines, which suggests that familial transmission of this virus is likely to occur.

ATLV is a pathogen for adult T cell leukemia. This finding stems from the success of the present inventor and his colleagues in cultivating an adult T cell leukemia cell strain, designated MT-1 cells, from the peripheral blood of an adult T cell leukemia patient. As a result of a joint study by this inventor and other researchers, it was found that an antigen exist in this cell strain which specifically reacts with and is intimately associated with adult T cell leukemic serum and C-type viral particles or virious. This antigen was thus tentatively named the "adult T cell leukemia associated antigen (ATLA)".

The following literature references give details about these findings.

(1) Miyoshi, I. et al.: Gann, 71: 155, 1980

(2) Miyoshi, I. et al.: Jap. J. Clin. Oncol., 9 (Suppl.): 485, 1979

(3) Hinuma, Y. et al.: Proc. Nat. Acad. Sci., 78: 6476, 1981.

At nearly the same time as the discovery of ATLA, Gallo et al. in the United States succeeded in deriving a T cell strain from mycosis fungoides and Sézary syndrome patients by using a T cell growth promoting factor, and disclosed their discovery of a C-type retrovirus (HTLV) in the cultured cells.

*Mycosis fungoides*, Sézary syndrome and adult T cell leukemia are diseases which are clinically akin to each other, and the fact that a C-type virus found in the cultured cells by Gallo et al. was considered to be an etiological factor in certain kinds of T cell associated tumors in man.

The mechanism of transmission of ATLV is not completely understood, but in view of the fact that many antibody-positive persons are found in the same family and that the antibody positiveness ratio is high among married couples, it is considered probable that the virus is transmitted from mother to child through fetation, parturition or breast feeding, or is transmitted by horizontal transmission due to physical contact between married couples.

The present inventor and his colleagues have verified that some adult T cell leukemia associated antibody-positive persons are blood transfusion donors, and such donors could carry ATLV. That is, there is a possibility that blood transfusions could play a very important role in the transmission of ATLV. Also, the fact that adult T cell leukemia associated antibody-positive persons are found among persons who have received blood transfusions frequently in connection with diseases other than the adult T cell leukemia suggests the possibility that ATLV is transmitted through blood transfusion. The following literature references disclose findings verifying or relating to these facts.

(4) Miyoshi, I. et al.: Gann, 73; 339,1982

(5) Miyoshi, I. et al.: Lancet: 683, 1982

(6) Shimoyama, M. et al.: Jap. J. Clin. Oncol. 12: 109, 1982.

Under these circumstances, urgent measures need to be taken to check whether a blood donor carries adult T cell leukemia associated antibodies and to thereby prevent viral infection of blood transfusion from such an antibody-positive person. For this purpose, it is essential that a method for assaying adult T cell leukemia associated antibodies, with high sensitivity, is established, and that a method is achieved for high-yield production of an adult T cell leukemia associated antigen, especially a high active one, which is necessary for the practice of such an assay. It is also desirable to furnish a preliminarily prepared reagent for facilitating the practice of this assay.

In the prior art, a method is known for assaying adult T cell leukemia associated antibodies by an indirect fluorescent antibody technique. According to this method MT-1 or MT-2 cells, which are adult T cell leukemia associated antigen producing cells, are smeared, air-dried and acetone-fixed on a glass slide, and then a specimen is reacted therewith. This method, however, requires a special apparatus, requires that the person carrying out the test has a great deal of skill, is incapable of treating a large number of specimens at once, and is also poor in detection sensitivity.

Under these circumstances, the present inventor has conducted extensive research, and as a result has found that a practical method for assaying adult T cell leukemia associated antibodies can be attained. According to this method, an adult T cell leukemia associated antigen is produced by treating adult T cell leukemia associated antigen producing cells with a surfactant, and then performing enzyme immunoassay, radioimmunoassay or passive hemagglutination on a blood serum sample from a subject, using this antigen as a test reagent. This is disclosed in Japanese patent application No. 169 670/82, U.S. patent application Ser. No. 535,457, Sept. 23, 1983, now U.S. Pat. No. 4,588,681, and EPC patent application No. 83 109 691.2, now EPC patent publication A2 No. 105465.

However, it is desirable that adult T cell leukemia associated antibodies are produced in a large scale for a more detailed diagnosis of adult T cell leukemia. For example, it would be possible to detect and determine adult T cell leukemia associated antigen by using antiserum of any convenient animal, if said animal could be made to produce adult T cell leukemia associated antibodies.

However, since currently available adult T cell leukemia associated antigen producing cells such as MT-2 cells are a cell strain obtained from a mixed culture of leukemia cells collected from peripheral blood of an adult T cell leukemic human patient and human umbilical cord leukocytes, it is impossible to obtain only such antibodies that exhibit an immunologically high specificity to human adult T cell leukemia associated antigen by directly inoculating said cell strain into an animal other than human or ape. Consequently, it is necessary to establish a special solution to induce an animal other than human or ape to produce adult T cell leukemia associated antibodies. The present inventor has conducted researches to examine the above mentioned solution, and as a result found that a cell strain obtained from a mixed culture of leukocytes of an animal other than human or ape and adult T cell leukemia associated antigen producing cells which exhibit an immunologically high specificity to said animal when inoculated into said animal, leading to the achievement of the present invention.

That is to say, it is an object of this invention to produce adult T cell leukemia associated antibodies by inoculating a cell strain into an animal other than human or ape. To achieve the above mentioned object, this invention provides a novel cell strain, a process for producing it characterized by a mixed culture of leukocytes of said animal and adult T cell leukemia associated antigen producing cells and a process for producing antiserum characterized by inoculating said cell strain to the corresponding animal.

The invention will now be described in detail.

The term "adult T cell leukemia associated antigen" is used herein to refer to antigenic proteins and C-type virions present in a culture of leukemia cells collected from the peripheral blood of an adult T cell leukemic patient and typified by a specific antibody-antigen reaction with adult T cell leukemia antibodies in adult T cell leukemia patient blood serum. The antigenic protein is composed of proteins having different molecular weights, principally those having a molecular weight of about 24,000. The term "C-type virion" refers to an RNA virion having a reverse transcriptase activity. Its shape is spherical, as observed under an electron microscope, and its density, as measured by the sucrose gradient centrifugation method, is 1.152 to 1.155 g/cm$^3$. Further particulars, including the properties of the adult T cell leukemia associated antigen, are disclosed in the following literature reference.

(7) Yoshida M, et al.: Proc. Nat. Acad. Sci., 79: 2031, 1982.

The term "adult T cell leukemia associated antigen producing cell" as used herein includes all cell strains that can produce the above-defined adult T cell leukemia associated antigen. Cells which fall in this class and are now available include cells of a series of cultured cell strain generally identified as MT-1, MT-2, MT-3 and MT-4 cells. These cultured cell strains have been established and available methods for obtaining these cells have been previously published by the present inventor and his colleagues. It was found that among them, the MT-2 cells are the most advantageous from the viewpoint of mass production of ATLV. Thus MT-2 cells, which are a typical example of adult T cell leukemia associated antigen producing cells, will be described in detail.

MT-2 cells are a cell strain derived from umbilical cord leukocytes obtained from a mixed culture of leukemia cells of an adult T cell lekemia human female patient and umbilical cord leukocytes of a normal, non-leukemic, human male neonate. The karyotype of MT-2 cells is 46, XY. An MT-2 cell is considered to result from transduction of an adult T cell leukemia virus genome from a leukocyte cell of the patient into an umbilical cord leukocytes of the neonate. MT-2 cells grow to form rosettes with sheep red blood cells, and react with monoclonal antibodies specific to human T cells. MT-2 cells are negative to EB virus nucleus antigen. The following literature references further describe the properties and method of obtaining MT-2 cells.

(8) Miyoshi, I. et al.: Gann, 72: 978, 1981
(9) Miyoshi, I. et al.: Nature, 294: 770, 1981.

Any animal other than human or ape may be used for immunizing in the present invention. Rabbit or hamsters are used in general.

Leukocytes of the selected animal are prepared as follows. 10 ml of the peripheral blood of said animal is collected and leukocytes are separated from the peripheral blood by a specific gravity centrifugation with Ficoll Hi-pac ®. Then they are previously cultured in a Petri dish for two days at a concentration of $1 \times 10^6$ cells/ml prior to the mixed culture which will be described hereinafter. A culture solution may be prepared by adding 10% of human umbilical cord serum, 10% of bovine fetal serum, 100 μg/dl of streptomycin and 100 u/ml of penicillin to RPMI 1640. The mixed culture may be carried out, for example, in the following manner.

To the leukocytes prepared in the above mentioned manner, adult T cell leukemia associated antigen producing cells which have been previously irradiated with X-ray (e.g. $1 \times 10^6$ of MT-2 cells irradiated with a dose of 10,000 R) are added and the mixture is cultured at 37° C. with a $CO_2$ concentration of 7.5%. Fresh culture solution is added at a frequency of twice a week. Two weeks after initiation of the mixed culture, clusters are formed increasing in number and size as the day goes on. Four weeks after mixing, the cultured cells may be transferred into another Petri dish and the culture is allowed to continue.

A culture solution for the mixed culture may be prepared, for example, by adding 20% of bovine fetal serum to RPMI 1640. While the invention has been described in its preferred embodiments, it is to be understood that the invention is not limited thereto but various modifications in irradiation dose with X-ray, culturing conditions and composition of medium may be made therein without departing from the spirit and scope of the invention.

The cell strain obtained from said mixed culture exhibit an intense vitality. That is to say, either of leukocytes of said animal or MT-2 cells irradiated with X-ray would perish within two months, while the cell strain obtained from the mixed culture would survive six months after initiation of the mixed culture.

The present inventor has selected a male rabbit (Japanese white species) as an animal other than human or ape and MT-2 cells as adult T cell leukemia associated antigen producing cells. The resulting cell strain from a mixed culture of the two was named Ra-1 cells. The properties of the Ra-1 cells, which are a typical example of a cell strain of the present invention, will be described in detail hereinafter.

Almost all of Ra-1 cells are lymphoblasts which are negative to peroxidase reaction, multiply in a suspended state and double themselves within approximately 30 hours. Ra-1 cells have no surface immunoglobulin receptor for, sheep red blood cell, Fc part of IgG nor receptor for complement, and do not react with monoclonal antibodies to human T cell antigen (Leu-1, Leu-2 and Leu-3a) nor Ia antigen (OKI 1). The chromosome number thereof is 44, exhibiting a male rabbit species.

Under an electron microscope, C-type virions are observed outside of Ra-1 cells. These virions have the same shape as that of adult T cell leukemia virus, a diameter of 100 to 150 nm and are composed of a nucleoid and external membrane.

A conventional immunizing method for aimals may be carried out to produce the antiserum concerning the present invention by using a cell strain of the present invention. For example, said Ra-1 cells are intravenously inoculated into a rabbit or the like frequently at fixed intervals of time and its blood is collected after a certain period of time to obtain the serum.

As shown in Example 2 described below, the antiserum concerning the present invention would specifically react with adult T cell leukemia associated antigen positive cells, and would not react with any other general human leukemic cells. The behavior thereof in said reaction is similar to that of adult T cell leukemic serum. Consequently, it has been found that a process and cell strain of the present invention are capable of achieving the object of the present invention (i.e. to produce adult T cell leukemia associated antibodies by using an animal other than human or ape). More concretely, it has been found that the present invention makes it possible to inoculate a cell strain suitable for producing adult T cell leukemia associated antibodies into an animal other than human or ape.

To further illustrate the present invention, the following examples are given.

EXAMPLE 1

10 ml of the peripheral blood was collected from a male rabbit (Japanese white species) and leukocytes were separated by a specific gravity centrifugation with Ficoll Hi-pac ®. Then they were cultured in a Petri dish for two days at a concentration of $1 \times 10^6$ cells/ml. The culture solution was prepared by adding 10% of human umbilical cord serum, 10% of bovine fetal serum, 100 μg/dl of streptomycin and 100 μ/ml of penicillin to RPMI 1640.

Then $1 \times 10^6$ of MT-2 cells which had been irradiated with a dose of 10,000 R were added, and cultured at 37° C. in a $CO_2$ concentration of 7.5% for four weeks. During this culturing, fresh medium was added with a frequency of twice a week.

Then the mixed culture was transferred into a new medium which was prepared by adding 20% of bovine fetal serum to RPMI 1640 and allowed to continue for four months to obtain adult T cell leukemia associated cell strain Ra-1.

EXAMPLE 2

$5 \times 10^7$ of the Ra-1 cells obtained in Example 1 were intravenously inoculated into a male rabbit (Japanese white species). After two weeks, $5 \times 10^7$ of Ra-1 cells were intravenously inoculated into said animal again. Its blood was collected one week after the first inoculation, one and two weeks after the second inoculation to obtain adult T cell leukemia associated antisera a, b and c, respectively.

Antibody titers of a, b and c determined by an indirect fluorescent antibody technique were X80, X160 and X320, respectively. All of the three antiserums reacted with adult T cell leukemia associated antigen producing cell strains MT-2 (human), Si-1 (ape) and Ra-1 (rabbit). On the contrary, they did not react with three ATLV negative human leukemic cell strains (i.e. TALL-1, BALL-1 and NALL-1). Si-1, TALL-1, BALL-1 and NALL-1 are described in the following literature references.

(10) Miyoshi, I. et al. Lancet 1, 1061 (1982)
(11) Miyoshi, I. et al. Nature 267, 843–844 (1977).

In addition, a, b and c not only react with marginal cytoplasm of fixed Ra-1 cells, but with surface membrane of viable Ra-1 cells. These behaviors coincide with that of adult T cell leukemia sera which react with both of fixed and viable cells which are positive to adult T cell leukemia associated antigen.

The embodiments of the invention in which an exclusive property or privilege is claimed are defined as follows:

1. An adult T cell leukemia associated cell strain obtained from a mixed culture of leukocytes of a rabbit and adult T cell leukemia associated antigen producing cells, said cell strain being characterized by having cells which are derived from a rabbit and have a chromosome number of 44, are lymphoblasts which are negative to peroxidase reaction, have no surface immunoglobulin, no receptor for sheep red blood cells, no receptor for Fc part of IgG and no receptor for complement, do not react with monoclonal antibodies which bind to human T cell antigens Leu-1 or Leu-2 or Leu-3a or Ia antigen OKI 1 and have C-type virions outside the cells which have the same shape as that of adult T cell leukemia virus, said virions having a diameter of 100 to 150 nm and being composed of a nucleoid and an external membrane.

2. An adult T cell leukemia associated cell strain as set forth in claim 1, in which said adult T cell leukemia associated antigen producing cells are MT-2 cells.

3. An adult T cell leukemia associated cell strain as set forth in claim 1 which is 44 and is derived from a male rabbit.

4. A process for producing an adult T cell leukemia associated cell strain which can be used for immunizing a rabbit, comprising culturing a mixture of leukocytes of said rabbit and adult T cell leukemia associated antigen producing cells for a time and under conditions effective to produce a recoverable quantity of a cell strain as claimed in claim 1, and recovering said cell strain.

5. A process for producing an adult T cell leukemia associated cell strain as claimed in claim 4, in which said adult T cell leukemia associated antigen producing cells are MT-2 cells.

6. A process for producing an adult T cell leukemia associated antiserum, comprising: inoculating an adult T cell leukemia associated cell strain as claimed in claim 1, or claim 2, into a rabbit, to produce the antiserum in the blood of the rabbit and recovering, from the inoculated rabbit an antiserum which binds to cells of an adult T cell leukemia associated cell strain.

7. A process for producing an adult T cell leukemia associated antiserum, comprising: inoculating an adult T cell leukemia associated cell strain as claimed in claim 2, into a rabbit, to produce the antiserum in the blood of the rabbit and recovering, from the inoculated rabbit, an antiserum which binds to cells of an adult T cell leukemia associated cell strain.

* * * * *

UNITED STATES PATENT AND TRADEMARK OFFICE
CERTIFICATE OF CORRECTION

PATENT NO. : 4 792 524

DATED : December 20, 1988

INVENTOR(S) : Isao MIYOSHI

It is certified that error appears in the above-identified patent and that said Letters Patent is hereby corrected as shown below:

Column 6, line 52; delete "is 44 and".

Signed and Sealed this

Twenty-fourth Day of October, 1989

Attest:

DONALD J. QUIGG

Attesting Officer

Commissioner of Patents and Trademarks